United States Patent
Affeld

[19]

[11] Patent Number: 5,980,568
[45] Date of Patent: Nov. 9, 1999

[54] MECHANICAL HEART VALVE

[76] Inventor: Klaus Affeld, Spandauer Damm 130, 14050 Berlin, Germany

[21] Appl. No.: 08/799,022

[22] Filed: Feb. 10, 1997

[30] Foreign Application Priority Data

Feb. 10, 1996 [DE] Germany ................. 196 04 881

[51] Int. Cl.$^6$ ............................................. A61F 2/24
[52] U.S. Cl. ........................... 623/2; 623/1; 623/66; 623/900; 137/527; 137/527.8
[58] Field of Search ................ 623/1, 2, 66, 900; 137/527, 527.8

[56] References Cited

U.S. PATENT DOCUMENTS

| 15,192 | 6/1856 | Peale | 623/2 |
|---|---|---|---|
| Re. 30,507 | 2/1981 | Kaster | 623/2 |
| 1,306,391 | 6/1919 | Romanoff | 623/2 |
| 4,021,863 | 5/1977 | Woien | 623/2 |
| 4,546,499 | 10/1985 | Possis et al. | 623/1 |
| 4,775,378 | 10/1988 | Knoch et al. | 623/2 |
| 4,787,901 | 11/1988 | Baykut | 623/2 |
| 4,923,465 | 5/1990 | Knoch et al. | 623/2 |
| 4,950,287 | 8/1990 | Reif | 623/2 |
| 5,064,432 | 11/1991 | Reif | 623/2 |
| 5,522,886 | 6/1996 | Milo | 623/2 |
| 5,641,324 | 6/1997 | Bokros et al. | 523/2 |

Primary Examiner—Mickey Yu
Assistant Examiner—Choon P. Koh
Attorney, Agent, or Firm—Fulbright & Jaworski L.L.P.

[57] ABSTRACT

The invention relates to a mechanical heart valve for artificial blood pumps and conduits. An occluder is located in a flow channel with an S-shaped center line and with a cross sectional area which decreases in the flow direction. The occluder is made in the form of a rotational body which can be turned around a pivot or virtual axis, which is located outside the center of gravity of the rotational body.

7 Claims, 1 Drawing Sheet

MECHANICAL HEART VALVE

BACKGROUND OF THE INVENTION

1. Field of the Invention

The invention relates to a mechanical heart valve for use as an artificial heart or heart support system or for use in artificial conduits as are implanted for a connection of the left cardiac chamber to the aorta.

2. Description of Related Art

An artificial mechanical heart valve is designed to release the blood flow in one direction and close it off in the reverse direction. In doing so it should clear an open cross section as large as possible, if the pressure upstream is greater than downstream. In this phase the occluder, the movable element of the mechanical heart valve, should offer as little resistance as possible to the blood flow. If this pressure relationship is reversed by the action of the heart, the mechanical heart valve will quickly close off this cross section to prevent backflow of a larger amount of blood.

The materials which are available for building this mechanical heart valve are much inferior to natural substances from which the body makes the blood-carrying components. Artificial materials can cause formation of blood clots which can hinder the function of the mechanical heart valve or also can close off blood vessels farther downstream. Besides material properties, these processes are furthermore also largely determined by the blood flow through the heart valve. Stagnation areas in which the blood moves only little or even circularly are especially disadvantageous. In technical terms these areas are flow separations and they form mainly when the flow cross section is widened or has recesses, edges and depressions. Also components which project into the flow, such as occluders, clips, axles or supports on their downstream side are associated with the danger of flow separation.

Numerous mechanical heart valves are known in which attempts are made to avoid flow separation by means of streamlined occluders.

Furthermore, mechanical heart valves are known in which the cross section in the area of their retaining ring decreases in the flow direction, so that in the area of the journal mounting accelerated flow prevails and thus the danger of flow separation is reduced. However, the area of accelerated flow extends only for a short region and does not include the entire area of the heart valve.

It is common to all these mechanical heart valves that the occluder during the flow-through phase is fixed in its angular position by stops. Usually the angle of attack of the occluder to the flow is so large that the flow separates on one side of the occluder and thus flow separation occurs.

It is furthermore common to all these known mechanical heart valves that flow separation on the rear edge of their retaining ring is inevitable because the flow cross section is widened here. The consequence is that all mechanical heart valves which are made of material which is not optimally compatible with blood are associated (this applies to all mechanical heart valves) with a certain rate of thromboembolic complications which then endanger the patient.

These mechanical heart valves have been developed for replacement of diseased natural hearts and are matched to the geometry of the natural flow channels found beforehand, for example, the aortic root. In artificial blood pumps on the other hand for the valves an anatomically defined geometry is not stipulated and the flow channels can be configured freely around the occluder. The same applies to conduits which are clinically used for a connection of the cardiac chamber to the aorta.

SUMMARY OF THE INVENTION

The object of the invention is to avoid the aforementioned disadvantages of the existing designs, such as flow separation, and to achieve the existing object in a technically superior manner.

The objectives of the invention are achieved by providing a mechanicals valve for controlling the flow of blood having an elongated flow channel with an inflow end and an outflow end in fluid communication. The flow channel is provided with a curved portion defining an S-shaped center line between the inflow end and the outflow end. An occluder is pivotally mounted within the curved portion of the flow channel. In operation, when the flow of blood pivots the occluder into the open position, the occluder does not extend beyond the inflow end or the outflow end of the flow channel. In other words, the occluder remains completely housed within the flow channel at all times.

The flow throughout the area of the mechanical heart valve is thus guided as claimed in the invention such that the cross section of the flow channel is always reduced and not widened, especially the area of the occluder also being included. The disk-shaped occluder can be supported by clips or projections and stops in known and proven ways.

The advantages achieved with the invention consist especially in that the flow is guided such that flow separation is prevented in the entire area of the mechanical heart valve.

The invention is detailed using the drawings.

DETAILED DESCRIPTION OF THE PREFERRED EMBODIMENTS

Figure 1:
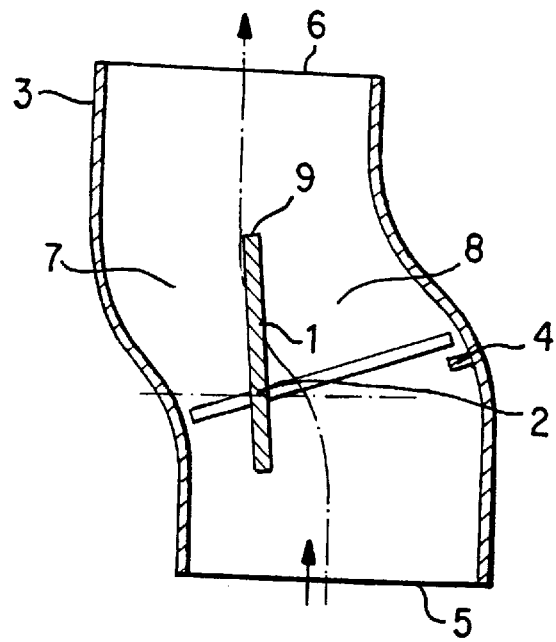
FIG. 1 shows a schematic of the mechanical heart valve in a longitudinal cross section.

Occluder 1 is a flat body of revolution which is supported in a journal 2 at roughly one third of its diameter or is pivotally mounted around virtual axis of rotation by a structure which is not detailed here or which is known in principle. Occluder 1 has stop 4 which prevents it from moving further in the closed state. In the open position occluder 1 does not have a stop and can thus be freely set in its angular position and can completely match the flow. Occluder 1 is located in flow channel 3 with a cross section which decreases steadily from inflow 5 to outflow 6. In this way accelerated flow which prevents the formation of flow separation is achieved. The arrangement of the virtual axis of rotation perpendicular to and outside of the axis of symmetry of occluder 1 causes the flow channel in the area of occluder 1 to be divided into area 7 with greater resistance and area 8 with less resistance. The two flows combine on the rear edge of occluder 1. The different speeds here lead to formation of eddy layer 9 which breaks down further downstream into small eddies. The free mobility of occluder 1 however prevents formation of flow separation. Furthermore, flow channel 3 has a center line curved into an S-shape. This shape of the curvature is necessary for closing of the occluder 1. If at the end of the flow through phase the flow has come to rest and backflow begins, the flow behaves like in a frictionless liquid. Boundary layers and velocity profiles have not yet formed here.

Figure 2:
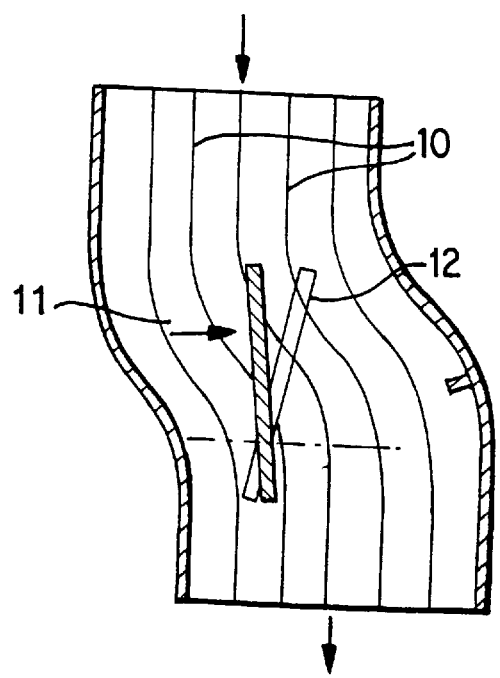
FIG. 2 shows the representation as in FIG. 1, likewise in longitudinal cross section, in the area of the heart valve the flow lines being shown at the start of the backflow phase.

FIG. 2 shows the arrangement of the flow lines of the flow at the start of the backflow phase. Flow lines 10 run through the plan of occluder 1 and in the initial phase thus have component 11 perpendicular to the axis of rotation of occluder 1 which exerts a torque on the occluder. Thus the flow entrains occluder 1 and continues to turn it somewhat into the flow into position 12, by which the entrainment effect is further intensified and the valve quickly moves into the closed portion as far as stop 4.

What is claimed is:

1. A mechanical heart valve for controlling the flow of blood comprising:

a flow channel for carrying blood having an inflow end and an outflow end in fluid communication, said flow channel having a curved portion between said inflow end and outflow end defining an S-shaped center-line;

an occluder pivotally mounted within the curved portion of said channel;

a stop operationally positioned within said channel such that a forward flow of blood pivots said occluder into an open position wherein the occluder is in a generally axial alignment with said outflow end and such that a backflow of blood pivots said occluder into a closed position wherein said occluder is in abutment with said stop;

wherein when said occluder is in the open position said occluder does not extend beyond said inflow end or said outflow end.

2. The mechanical heart valve of claim 1, wherein said channel has a cross-section of diminishing area along the length of the channel from the inflow to the outflow.

3. The mechanical heart valve of claim 1, wherein said occluder is acentrically pivot-mounted within said channel.

4. A mechanical heart valve for controlling the flow of blood comprising:

an annular flow channel for carrying blood having an inflow end and an outflow end in fluid communication, whereby a forward flow of blood travels from said inflow end towards said outflow end and a backflow travels from said outflow end towards said inflow end, said flow channel having a curved portion between said inflow end and outflow end defining an S-shaped center-line;

a disc-shaped occluder capable of restricting the flow of blood through the channel disposed within the curved portion of said channel, said occluder being acentrically pivot-mounted to said chamber;

a stop operationally positioned within said chamber such that a forward flow of blood pivots said occluder into an open position wherein the occluder is in a generally axial alignment with said outflow end and such that a backflow of blood pivots said occluder into a closed position wherein said occluder is in abutment with said stop;

wherein when said occluder is in the open position said occluder does not extend beyond said inflow end or said outflow end.

5. The mechanical heart valve of claim 4, wherein said channel has a cross-section of diminishing area along the length of the channel from the inflow to the outflow.

6. The mechanical heart valve of claim 5, wherein when said occluder is in an open position the occluder defines a flow passage one side having greater resistance than on the opposite side.

7. The mechanical heart valve of claim 5, wherein the flow passage having greater resistance causes the backflow of blood to create a torque that pivots the occluder in the direction of the stop.

\* \* \* \* \*